United States Patent [19]
De Bernardis

[11] Patent Number: 5,421,336
[45] Date of Patent: Jun. 6, 1995

[54] METHOD FOR ATTACHING AN INTERVENTIONAL MEDICAL DEVICE TO A VIBRATORY MEMBER ASSOCIATED WITH VISUALIZATION BY AN ULTRASOUND IMAGING SYSTEM

[75] Inventor: Francis A. De Bernardis, Ridgewood, N.J.

[73] Assignee: Echo Cath, Inc., Monmouth Junction, N.J.

[21] Appl. No.: 222,716

[22] Filed: Apr. 4, 1994

[51] Int. Cl.⁶ .............................................. A61B 8/12
[52] U.S. Cl. ............................................... 128/662.05
[58] Field of Search ............... 128/660.03, 662.03, 128/662.05, 662.06; 73/599, 602

[56] References Cited

U.S. PATENT DOCUMENTS

| | | | |
|---|---|---|---|
| 4,469,106 | 9/1984 | Harui | 128/662.05 |
| 4,869,259 | 9/1989 | Elkins | 128/662.02 |
| 5,052,396 | 10/1991 | Wedel et al. | 128/662.05 |
| 5,076,279 | 12/1991 | Arenson et al. | 128/662.05 |
| 5,235,987 | 8/1993 | Wolfe | 128/662.05 |
| 5,329,927 | 7/1994 | Gardineer et al. | 128/660.03 |

*Primary Examiner*—George Manuel
*Attorney, Agent, or Firm*—Plevy and Associates

[57] ABSTRACT

An ultrasonic imaging system comprising an interventional device having a key member: a vibrator member coupled to the interventional device for transmitting a vibratory mechanical oscillation in the form of flexural waves to the interventional device, to cause the interventional device to produce a motion according to the flexural waves, the vibrator member including a lock member which cooperates with the key member to assure firm attachment of the interventional device to the vibrator member; and an ultrasonic imaging system which detects the motion of the interventional device and generates an image of an interior of a body in which the motion is locatively represented.

1 Claim, 5 Drawing Sheets

METHOD FOR ATTACHING AN INTERVENTIONAL MEDICAL DEVICE TO A VIBRATORY MEMBER ASSOCIATED WITH VISUALIZATION BY AN ULTRASOUND IMAGING SYSTEM

RELATED APPLICATIONS

The assignee herein, EchoCath, Inc. is the record owner of U.S. Patent application entitled "APPARATUS AND METHOD FOR LOCATING AN INTERVENTIONAL MEDICAL DEVICE", Ser. No. 08/022,112 filed on Feb. 25, 1993 for Bayard Gardineer et al.

FIELD OF THE INVENTION

The present invention relates to ultrasound imaging systems and more particularly, to a method for attaching biopsy needles or other interventional devices of varying diameters to a mechanical motion mechanism used in conjunction with a color ultrasonic imaging system.

BACKGROUND OF THE INVENTION

At present, physicians can view internal regions of the body using well known ultrasonic imaging techniques. Procedures, for example, which utilize ultrasonic imaging techniques, include the biopsy of potentially malignant tumors. The biopsy procedure utilizes an interventional medical device, such as a biopsy needle, which the physician inserts into the body of a patient. The physician guides the biopsy needle toward the tissue to be biopsied by watching an image of an internal region of the body produced by the ultrasonic imaging system. During this procedure, it is supremely important for the physician to be able to clearly visualize the needle while guiding it through the patient's body toward the area of tissue to be removed by the biopsy needle, as the needle can bend off the intended path and pierce vital organs.

Ultrasonic imaging techniques may also be used in other procedures to monitor the placement of other types of medical instruments including trocars, catheters, etc., within the body.

The prior art includes a number of methods for monitoring the path of medical devices as they are directed through the body of a patient. For example, the insertion path of a catheter can be monitored using ultrasonic imaging techniques. In U.S. Patent No. 4,697,595 issued to Breyer et al., a cardiac catheter and its associated pacing leads, which carry one or more ultrasonic transducers, are used in combination with an ultrasonic imaging system. The catheter or the leads are represented inside the body as an ultrasonic image by reception or transmission of ultrasonic signals between the imaging transducer and the transducer mounted on the pacing leads. Another method is found in U.S. Pat. No. 5,076,278 issued to Vilkomerson et al. The '278 patent discloses an annular ultrasonic transducer that is sensitive over a broad range of angles of incident acoustic beams and which is mounted on a catheter or other medical device. By utilizing an ultrasonic imaging system, the position of the transducer on the catheter during ultrasonic scanning modes can be ascertained and incorporated into the image generated by the imaging system. This system, however, detects and displays only one point of the medical device.

Biopsy needles can also be monitored within the body using ultrasonic imaging techniques by providing the needle with an ultrasonic transducer in order to cause the needle to transmit and/or receive ultrasonic waves in cooperation with an imaging scanhead. For example, U.S. Pat. No. 3,556,079 issued to Omizo discloses a method whereby Doppler interrogating waves are directed forward from the tip of a biopsy needle. As the needle penetrates the body, backscatter waves from moving fluids within a vessel or organ are received and a conventional Doppler beat frequency is detected. The reception of the Doppler tone provides an indication that the needle is aimed at the vessel or organ containing the fluid. The Omizo method is a highly directional method and consequently, if the needle becomes misdirected, no backscatter waves will be returned thereby causing the Doppler tone to cease.

More recently in U.S. Pat. No. 4,249,539 issued to Vilkomerson et al., a system is disclosed which includes an omnidirectional transducer located at the needle tip. The transducer is used as a transponder to send signals back through the body to a transmitter when a signal is detected. The omnidirectional transducer exchanges ultrasonic waves with the imaging transducer irrespective of the orientation of the omnidirectional transducer, thus enabling the system to continually provide a visual marker in the ultrasonic image which indicates the needle tip location. An ultrasonic imaging transducer provides a two-dimensional image as it scans a relatively planar portion of the patient's body. Consequently, the needle tip can only be visualized when it is located within the scan plane of the imaging transducer. Hence, the '539 system cannot visualize the needle tip when the physician first enters the body if the plane of penetration is outside of the scan plane of the imaging transducer. When this occurs, the physician is required to focus his attention on the insertion and guidance of the biopsy needle and at the same time manipulate the imaging transducer and watch the imaging monitor to simultaneously orient the transducer and the needle so that the tissue structure to be biopsied and the needle tip are in the image or scan plane.

Most recently in U.S. Pat. No. 5,095,910 issued to Powers, a biopsy needle with a reciprocating tip that produces a highly directional motion is described. The highly directional motion produces a Doppler shift which is detected and displayed by a color ultrasonic imaging system. As a result, the needle tip can be monitored as it is guided toward the tissue to be biopsied. The biopsy needle in the '910 patent comprises an inner solid element or stylet which reciprocates longitudinally within a hollow tube or cannula. The only motion that appears in the ultrasonic colorflow image as a visual Doppler response is the motion of the tip of the stylet at the open end of the cannula. This motion is shown as color. The system will not show the tip of the stylet if the tissue is liquid in nature, such as in the necrotic center of tumors, or when the stylet tip is at right angles to the ultrasound beam. The reciprocating motion is provided by a driver in the hub of the needle. As such, this arrangement is limited to specially prepared needles or other such devices for use in this system.

It should also be mentioned that color imaging has also been utilized in ultrasound systems used to measure blood velocity. The prior art recognizes that moving blood cell reflect ultrasonic energy that is Doppler shifted in frequency. Therefore, the velocity of the blood may be measured by utilizing an ultrasound imaging system. Moreover, ultrasound imaging systems have been utilized to locate the best point in a blood vessel in which to measure blood velocity by measurement of the Doppler shift. The Doppler shift in backscattered ultrasound at a point in a blood vessel is measured by the detection of quadrature time samples of the backscattered signal. This technique entails the monodyne detection of the signal in conjunction with sine and cosine mixing at a transmitted frequency in order to detect real and imaginary parts of a signal vector at a sampling time. The signal vector, which is a sum of the individual signal vectors from each blood cell, changes slowly (assuming the blood cells stay in the same relative positions) but advances or retreats in phase depending upon whether the blood cells are coming toward a transducer or away.

In copending Patent application Ser. No. 08/022112, the disclosure of which is expressly incorporated herein by reference, the applicants describe a system in which the tip of a biopsy needle or other interventional medical device is visualized in the body of a patient using a color ultrasonic imaging system. Disclosed therein is an apparatus and method for causing a periodic or oscillating mechanical motion in the needle which results in a significant Doppler shift effect that enables the needle to be detected by the color ultrasonic imaging system. The needle or other interventional medical device is made to oscillate by a mechanical motion mechanism. The needle is coupled and secured to the mechanical motion mechanism using a flexible clip-like element formed for instance, from any suitable metal or plastic. The flexible clip-like element is designed to accommodate and secure needles of different gages to the mechanical motion mechanism. Current medical practice dictates the use of needles having gages ranging from 14 gage (2.0 mm in diameter) to 25 gage (0.4 mm in diameter). Problems, however, having to do with assured firm fixation of the needle to the mechanical motion mechanism still arise due to the fixed diameter of the flexible clip-like element. The selected diameter of the clip-like element results in a compromise which tends to favor needles in a given narrow gage range. Needle sizes falling at the outer ends of this range tend to fit less securely than needle sizes which fall within the given narrow range. Consequently, in cases where the needle fits less securely the mechanical motion transfer from the mechanical motion device to the needle results in ineffective operation of the imaging system.

It is therefore an object of the present invention to provide a method for firmly and consistently attaching needles of varying diameters to a mechanical motion mechanism used in a color ultrasonic imaging system which utilizes a lock having a fixed diameter.

SUMMARY OF THE INVENTION

An ultrasonic imaging system comprising an interventional device such as a biopsy needle, having a key member; a vibrator means coupled to the interventional device for transmitting a vibratory mechanical oscillation in the form of flexural waves to the interventional device, to cause the interventional device to produce a motion according to the flexural waves, the vibrator means including a lock member which cooperates with the key member to assure firm attachment of the interventional device to the vibrator means; and an ultrasonic imaging system including means for detecting the motion of the interventional device and means for generating an image of an interior of a body in which the motion is locatively represented.

The key member and the lock member of the ultrasonic imaging system are similarly shaped to cooperate with each other to provide maximum contact between the vibrator means and the interventional device. The lock member can be unitarily formed in the vibratory means or be a separately formed removable member.

The interventional device further includes an insertion member, e.g., a stylet or cannula, having a given diameter, the key member being affixed to the insertion member. The key member includes a bore for receiving the insertion member therethrough, the bore being sized to receive the given diameter of the insertion member.

The interventional device is manufactured from a high strength to weight ratio material such as stainless steel, which leads to strong light needles that vibrate well.

DETAILED DESCRIPTION

Figure 1:
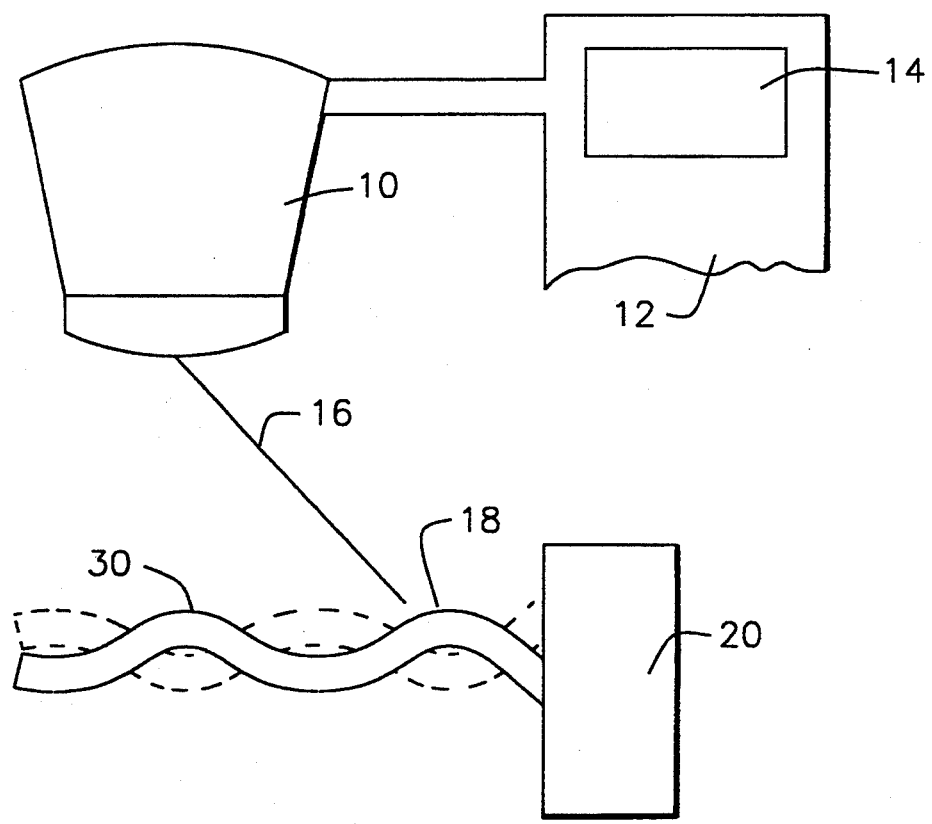
FIG. 1 is a schematic representation of a prior art ultrasound imaging system for transmitting mechanical motion to a biopsy needle.

Referring to FIG. 1, there is illustrated a simple block diagram of the operation of a prior art ultrasonic imaging system employing a prior art interventional device such as a biopsy needle. A detailed explanation of this system can be had by referring to U.S. patent application Ser. No. 08/022,112 the disclosure of which has been incorporated by reference. Briefly, FIG. 1 shows an ultrasound imaging scan head 10 that is coupled to an ultrasound imaging system 12 having a display 14. The scan head 10 is shown impressing an imaging pulse 16 on a point of a vibrating interventional device 30 of the present invention. The displacement of the device 30 is represented by phantom lines which are exaggerated for clarity. As an example of operation, the point 18 may be closest to the scan head 10 when the first imaging pulse 16 occurs and furthest when a second imaging pulse 16 occurs. Known imaging systems 12 are able to detect and display the velocity of a moving element in the 1–100 centimeters per second or more (cm/sec) range. In order to accomplish this, the first and second imaging pulses 16 of FIG. 1 are produced typically every 80 to 330 microseconds (usec) depending on the scale of the velocity to be detected. If a 5 cm/sec velocity is detected with a sampling interval of the imaging pulses set at 118 microseconds, the detected displacement of the point 18 is 5 centimeters/second times 118 microseconds, or approximately 6 microns. Therefore, as indicated above, small vibratory motions, on the order of microns, can be detected by known colorflow imaging systems.

As can be seen in FIG. 1, the biopsy needle 30 is coupled to a mechanical motion mechanism or VIBER mechanism 20. The term "VIBER" is a coined term used as a trademark by Echo Cath, Inc., the assignee herein, and is used to describe the mechanical motion mechanism 20. The VIBER mechanism 20 is capable of operating in at least one of a multiplicity of mechanical motion modes including modes able to transmit mechanical energy along one or more of the X, Y and Z axes of a device. The mechanical energy produced by the mechanical motion mechanism 20 causes the transmission of mechanical energy in the form of flexural waves to the interventional device 30. The term "flexure", is utilized to denote the curving or bent state of the needle which is produced by the wave-like characteristics of the mechanical energy transmission generated by the VIBER mechanism 20. Flexure occurs in an elastic structural material when a deflection is suitable to set-up stresses in the material. The flexural waves are vibratory flexural waves which may operate and exhibit characteristics similar to standing waves or as propagating waves. The flexural waves provided by the mechanical motion generation are transmitted about or along the X,Y and/or Z axes at synchronized, but non-harmonically related frequencies that correspond to resonant frequencies of the needle 30. As a result, the device 30 undulates in the flexural modes depicted in FIG. 1. between the solid and phantom lines. Accordingly, the ultrasonic imaging system 12, via the scanner 10, can detect Doppler movements resulting from undulations of the flexural waves in any of the X,Y and Z planes and provide a precise indication on the display 25 as to the location of the device 30 within the body of a patient.

Figure 4:
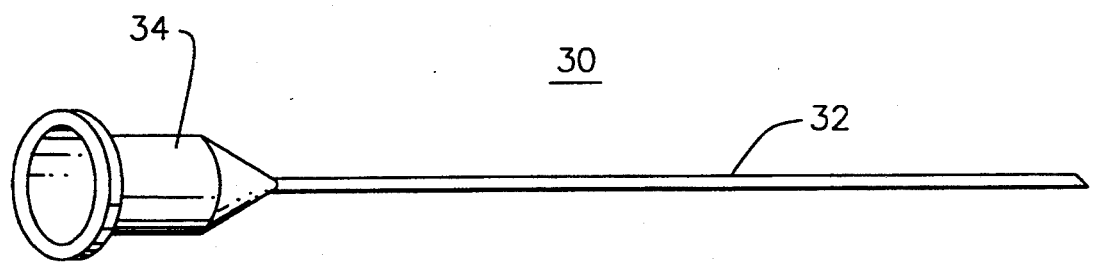
FIG. 4 is a planar representation of a prior art biopsy needle.

The prior an interventional device 30 seen in FIG. 4 is a biopsy needle. Biopsy needle 30 comprises a shaft portion 32 and a hub portion 34. The mass of the VIBER mechanism 20 must be much greater than the mass of the biopsy needle 30 in order to minimize the change in resonance frequency of the system when the needle 30 is attached. Thus, the biopsy needle 30 is constructed from stainless steel or any other suitable material which results in a low mass hub portion. Moreover the mass of the shaft portion 32 of the needle 30 is minimized by utilizing an extremely thin tube or cannula. Biopsy needles vary in diameter and in length and include many different styles of cutting tips. Biopsy needles typically range in gages from 16 (1.6 mm diameter) to 25 (0.4 mm diameter) and come in lengths from 0.5 inches to 10 inches.

Figure 2:
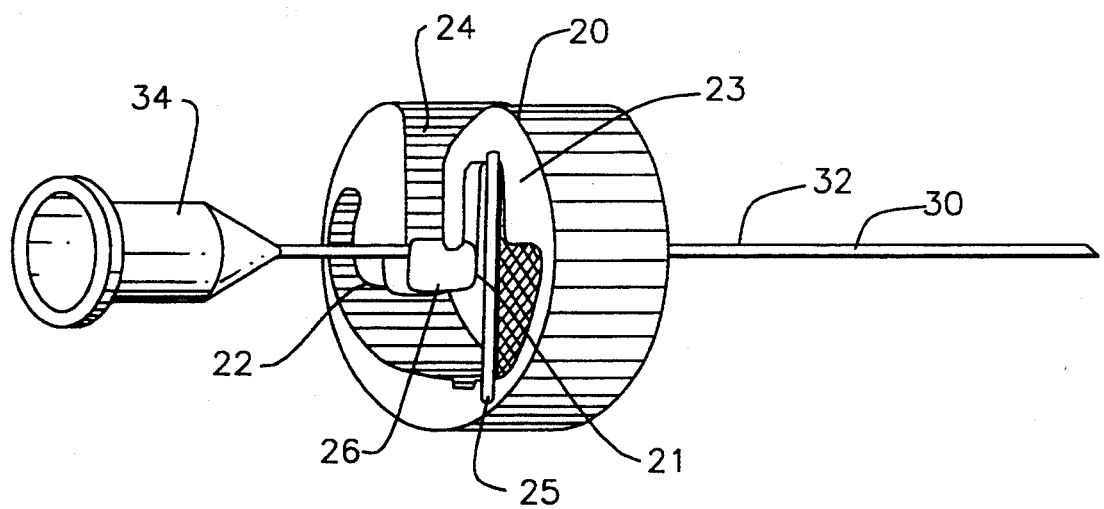
FIG. 2 is a planar representation of a prior art mechanical motion mechanism coupled to a prior art biopsy needle.

Referring now to FIG. 2, there is shown a detailed view of prior art interventional device 30 coupled to a VIBER mechanism 20. Device 30 is directed through and coupled to the mechanical motion mechanism 20 via a spring-like clip 26. The VIBER mechanism 20 is constructed from a suitable metal material such as brass, zinc, stainless steel and alloys of the same. The VIBER mechanism 20 is formed to a generally C-shaped configuration having an elongated peripheral slot 24 which is bounded on one side by a pendulum-shaped member 22 and on the other side by a section 23 arranged to mount one or more plate-shaped piezocrystal diaphragms 25. At least one of the piezocrystal diaphragms 25 is activated or excited by means of a suitable voltage source as is more thoroughly explained in patent application Ser. No. 08/022,112. A metal electrode plate 21 is one of many methods that can be utilized to couple the piezo-crystal diaphragm 25 to the voltage source.

Figure 3:
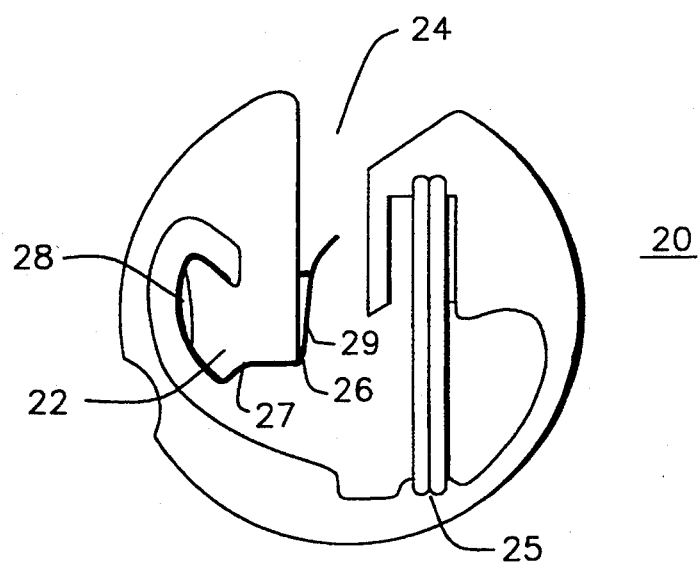
FIG. 3 is front view of the prior art mechanical motion mechanism and the spring mechanism associated with it.

The prior art spring-like clip 26 is best illustrated in FIG. 3. Clip 26 is mounted to the pendulum-shaped member 22 and is used to secure the device 30 to the VIBER mechanism 20. The clip 26 has a C-shaped profile defined by center portion 27 and upper and lower legs 28 and 29 respectively. Device 30 is coupled to VIBER mechanism 20 by inserting the shaft 32 of device 30 between the pendulum-shaped member 22 and the upper leg 28 of the clip 26. The spring-like characteristic of clip 26 was intended to allow interventional devices of varying diameters to be coupled to the VIBER mechanism 20. However, secure and effective attachment of needles with varying diameters to the VIBER mechanism 20 has remained a problem up until now. The present invention solves this problem by providing a key shaped element of a fixed dimension on the shaft of the interventional device, the key being adapted to fit the profile of an aperture or lock provided in a modified embodiment of the VIBER mechanism described above. A more detailed description of the key and lock assembly of the present invention follows below.

Figure 5:
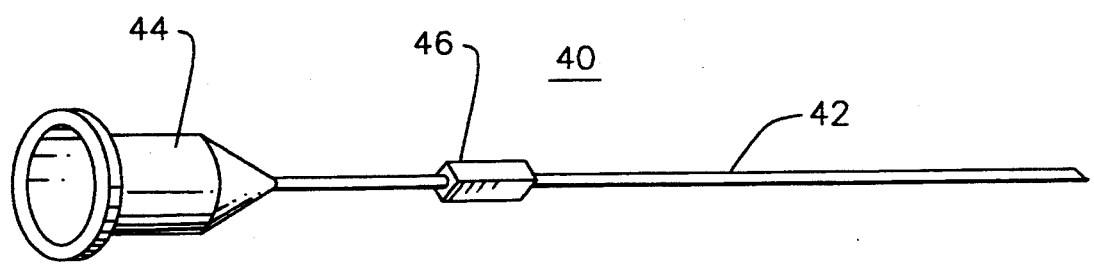
FIG. 5 is a planar representation of a biopsy needle according to an exemplary embodiment of the present invention.

Referring now to FIG. 5, there is shown an exemplary embodiment of an interventional device such as a biopsy needle according to the present invention designated by the numeral 40 which has been specifically designed for use with a modified VIBER mechanism used with the color ultrasonic imaging system described herein. Biopsy needle 40 of the present invention is constructed in much the same fashion as prior art needle 30 in that it includes a shaft portion 42, a hub portion 44, all formed from stainless steel or other suitable materials easily recognized by one of ordinary skill in the art. However, the needle according to the present invention further includes a low mass key shaped element 46 which is positioned adjacent to the hub portion 44. The key 46 presents an outer profile which remains the same regardless of the diameter, length or tip style of the biopsy needle. This allows biopsy needles of varying diameters to be assuredly attached to the VIBER mechanism 20. In accordance with the present invention, the profile of the key is adapted to fit the lock provided in a modified VIBER mechanism 20 which is described below in greater detail. The key 46 shown in FIG. 5 has a rectangular profile, however, it is noted that any suitable key shaped configuration is possible. The key 46 is further provided with a bore (not shown) which extends entirely through key 46 to receive the shaft 42 of the biopsy needle 40. The diameter of the bore is adapted to fit the particular diameter of the shaft to be used. The key 46 is fastened to the shaft using any well known method of attachment such as brazing, soldering, etc., so that the key 46 is prevented from sliding along the shaft 42 of the biopsy needle 40. It is also contemplated that the key 46 can be unitarily formed with the shaft 42. Because the outer dimension of the key 46 is fixed the shape of the key profile can be optimized as describe below, to securely attach the needle to the modified VIBER mechanism 20. Secure attachment ensures maximum transfer of mechanical energy from the VIBER mechanism to the biopsy needle which results in more effective operation of the color ultrasonic imaging system.

Figure 6:
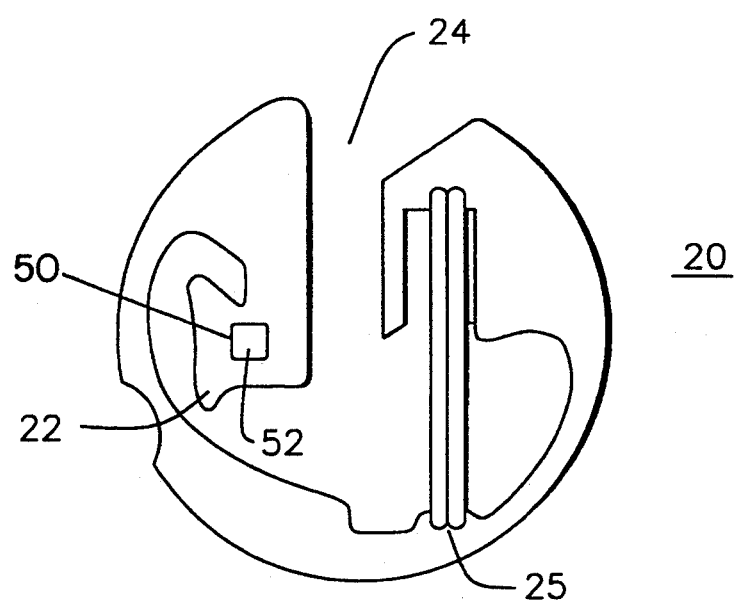
FIG. 6 is a front view of a unitarily formed lock in a mechanical motion mechanism according to an exemplary embodiment of the present invention.

The lock according to the present invention and designated by numeral 50 is unitarily provided in the pendulum-shaped member 22 as shown in FIG. 6. The lock 50 includes a square shaped aperture 52 which is adapted to securely receive and engage the key 46 of the biopsy needle 40. This arrangement assures firm attachment of the biopsy needle to the VIBER mechanism 20. The shape of the lock 50 is not limited to the shape shown in FIG. 6 and can be any shape which matches the profile of the key to be used.

Figure 7:
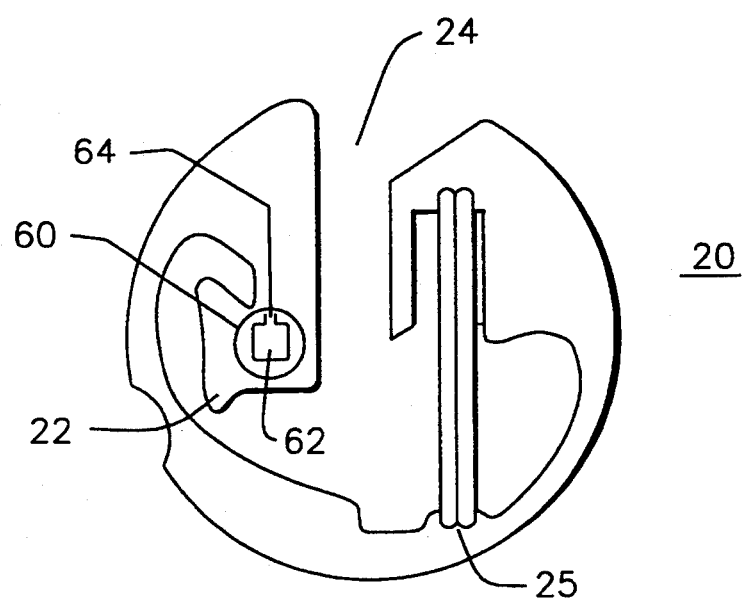
FIG. 7 is a front view of a lock in a mechanical motion mechanism according to another embodiment of the present invention.

In FIG. 7 there is shown another embodiment of a modified VIBER mechanism 20 wherein the lock is provided as a removable member designated by the numeral 60. The removable member can be formed from any suitable material, like metal, which displays good acoustical propagation characteristics. This is important for transferring the mechanical energy produced by the VIBER mechanism to the biopsy needle. Removable member 60 is substantially circular in shape and includes a square shaped lock 62 which is adapted to securely receive and engage the key 46 of the biopsy needle 40 as shown in FIG. 5. Member 60 is provided with a slot 64 which opens into the lock 62 and allows the lock 62 to expand slightly to receive the key 46 of the needle 40. It is of course understood that the shape of the lock 62 is not limited to the shape shown in FIG. 7 and can be any shape which suitably matches the profile of the key to be used. The pendulum-shaped member 22 of the VIBER mechanism 20 includes an aperture (not shown) for receiving and securely retaining the removable member and biopsy needle assembly therein.

It should be understood that the embodiments described herein are merely exemplary and many alternate embodiments, as well as additional embodiments will become apparent to those skilled in the art. For example, the lock and key mechanism of the present invention can be adapted to secure any cannula, stylet, or guide wire type device to a vibrating member where it is desirable to provide mechanical motion transfer from the vibrating member to the cannula, styler or guide wire. Another example where the lock and key mechanism can be implemented is in devices which include a vibrating element located within a hollow probe or the like, where the vibrating element is attached to a vibrating member which operates to transfer mechanical motion to the vibrating element within the hollow probe. Accordingly, such alternative and additional embodiments are to be construed as being within the spirit of the present invention, even though not explicitly set forth herein, the present invention being limited only by the content and scope of the claims appended hereto.

I claim:

1. An interventional device for use with a color ultrasonic imaging system, comprising:

a hollow stylet defining a surface contour and a rectangularly shaped member for removably coupling said interventional device to a vibrating member portion of the color ultrasonic imaging system, said member defining a portion of said stylet having a surface contour which is substantially different from said surface contour of said stylet, and said stylet extending through a longitudinally extending central bore defined in said member.

* * * * *

UNITED STATES PATENT AND TRADEMARK OFFICE
CERTIFICATE OF CORRECTION

PATENT NO. : 5,421,336
DATED : June 6, 1995
INVENTOR(S) : De Bernardis

It is certified that error appears in the above-identified patent and that said Letters Patent is hereby corrected as shown below:

Claim 1, Column 8, lines 25-26 after "vibrating" delete "member", penultimate word.

Signed and Sealed this

Fifth Day of September, 1995

Attest:

BRUCE LEHMAN

Attesting Officer

Commissioner of Patents and Trademarks